United States Patent
Buswell et al.

(10) Patent No.: US 11,883,347 B2
(45) Date of Patent: Jan. 30, 2024

(54) FALL ARRESTING LIFT MACHINE

(71) Applicants: Sheila M. Buswell, St. Louis, MO (US); Gregg A. Buswell, St. Louis, MO (US)

(72) Inventors: Sheila M. Buswell, St. Louis, MO (US); Gregg A. Buswell, St. Louis, MO (US)

( * ) Notice: Subject to any disclaimer, the term of this patent is extended or adjusted under 35 U.S.C. 154(b) by 416 days.

(21) Appl. No.: 17/097,862

(22) Filed: Nov. 13, 2020

(65) Prior Publication Data
US 2021/0137768 A1    May 13, 2021

Related U.S. Application Data

(60) Provisional application No. 62/934,913, filed on Nov. 13, 2019.

(51) Int. Cl.
*A61H 3/00* (2006.01)
*A61G 7/10* (2006.01)
(Continued)

(52) U.S. Cl.
CPC .............. *A61H 3/008* (2013.01); *A61B 5/112* (2013.01); *A61B 5/1117* (2013.01); *A61G 7/1007* (2013.01); *A61G 7/1048* (2013.01); *A61G 7/1051* (2013.01); *A61H 3/04* (2013.01); *A61G 2203/10* (2013.01); *A61G 2203/36* (2013.01); *A61H 2003/007* (2013.01); *A61H 2003/043* (2013.01); *A61H 2003/046* (2013.01); *A61H 2201/1207* (2013.01);
(Continued)

(58) Field of Classification Search
CPC .... A61H 3/008; A61H 3/04; A61H 2003/007; A61H 2003/043; A61H 2003/046; A61H 2201/1207; A61H 2201/1652; A61H 2201/5007; A61H 2201/5064; A61H 2230/625; A61H 2201/163; A61H 1/00; A61B 5/1117; A61B 5/112; A61G 7/1007; A61G 7/1048; A61G 7/1051; A61G 2203/10; A61G 2203/36; A61G 7/1086; A61G 2203/32; A61G 7/1015; A61G 7/1046; A61G 7/1065
See application file for complete search history.

(56) References Cited

U.S. PATENT DOCUMENTS 2,327,671 A * 8/1943 Rupprecht ............... A61H 3/04
                                                              482/67
2,625,202 A * 1/1953 Richardson ............. A61H 3/04
                                                              482/68
(Continued)

*Primary Examiner* — Garrett K Atkinson
(74) *Attorney, Agent, or Firm* — Charles McCloskey

(57) ABSTRACT

A fall arresting lift machine has a gantry upon casters, a power source upon the gantry, a drive with a motor upon the gantry in communication with the power source, a controller in communication with the motor and the power source, a vertical strap paying out from the drive motor, a harness upon the strap, and the harness is suitable for wearing by a user. The gantry includes feet, housings, uprights, elbows, braces, and a union. The harness has straps for over both shoulders of the user and a belt and inertial measurement units upon the straps. The drive and controller cooperate to assist a user to sit and to stand, and to detect abrupt acceleration typical of a fall, and arrest the fall. The casters swivel, or alternately select wheels remain in fixed orientation.

10 Claims, 2 Drawing Sheets

(51) Int. Cl.
*A61H 3/04* (2006.01)
*A61B 5/11* (2006.01)

(52) U.S. Cl.
CPC ............... *A61H 2201/1652* (2013.01); *A61H 2201/5007* (2013.01); *A61H 2201/5064* (2013.01); *A61H 2230/625* (2013.01)

(56) References Cited

U.S. PATENT DOCUMENTS

| | | | | |
|---|---|---|---|---|
| 3,252,704 | A * | 5/1966 | Wilson | A61G 7/1017 482/68 |
| 3,408,067 | A * | 10/1968 | Armstrong | A63B 22/02 472/91 |
| 3,778,052 | A * | 12/1973 | Andow | A61H 3/04 482/67 |
| 4,204,673 | A * | 5/1980 | Speer, Sr. | A63B 22/0292 601/40 |
| 4,733,858 | A * | 3/1988 | Lan | A63B 21/4047 482/53 |
| 5,020,560 | A * | 6/1991 | Turbeville | A61H 3/04 280/282 |
| 5,228,708 | A * | 7/1993 | Verdugo | A61H 3/04 280/200 |
| 5,314,390 | A * | 5/1994 | Westing | A63B 21/4034 601/36 |
| 5,333,333 | A * | 8/1994 | Mah | A61H 3/04 280/30 |
| 5,460,394 | A * | 10/1995 | Novi | A61G 7/10 482/68 |
| 5,526,893 | A * | 6/1996 | Higer | A61H 3/04 482/68 |
| 5,662,560 | A * | 9/1997 | Svendsen | A63B 71/0009 482/54 |
| 6,030,039 | A * | 2/2000 | Essler | A47C 15/008 600/38 |
| 6,302,828 | B1 * | 10/2001 | Martin | A61H 3/008 482/69 |
| 7,125,388 | B1 * | 10/2006 | Reinkensmeyer | A63B 69/0064 601/5 |
| 7,156,789 | B2 * | 1/2007 | Nativ | A63B 71/02 482/904 |
| 7,294,094 | B1 * | 11/2007 | Howle | A61H 3/00 482/69 |
| 7,354,382 | B1 * | 4/2008 | Warren, II | A61H 3/04 482/68 |
| 7,980,856 | B2 * | 7/2011 | Grabiner | A63B 24/00 434/258 |
| 9,155,343 | B1 * | 10/2015 | Robbins | A41F 9/002 |
| 9,301,899 | B2 * | 4/2016 | Amer | A63B 21/068 |
| 9,422,023 | B1 * | 8/2016 | Espenschied | B62K 19/00 |
| 9,713,439 | B1 * | 7/2017 | Wu | A61B 5/221 |
| 10,265,565 | B2 * | 4/2019 | Jue | A63B 69/0064 |
| 10,272,284 | B2 * | 4/2019 | Bellman | A61H 3/008 |
| 10,342,461 | B2 * | 7/2019 | Basta | A61B 5/1038 |
| 10,398,619 | B2 * | 9/2019 | Crombie | A63B 21/068 |
| 10,549,807 | B2 * | 2/2020 | Drossman | B62K 1/00 |
| 11,253,415 | B2 * | 2/2022 | McKay | A61H 1/0229 |
| 2003/0141692 | A1 * | 7/2003 | Perena | A61H 3/008 280/250.1 |
| 2004/0143198 | A1 * | 7/2004 | West | A61H 1/0262 601/5 |
| 2006/0229167 | A1 * | 10/2006 | Kram | A63B 21/4015 482/54 |
| 2012/0018249 | A1 * | 1/2012 | Mehr | A63B 69/0064 182/5 |
| 2014/0206503 | A1 * | 7/2014 | Stockmaster | A61H 3/008 482/4 |
| 2016/0256346 | A1 * | 9/2016 | Stockmaster | G16H 40/63 |
| 2016/0367429 | A1 * | 12/2016 | Dolce | A61H 3/008 |
| 2017/0027803 | A1 * | 2/2017 | Agrawal | A61B 5/1122 |
| 2017/0112705 | A1 * | 4/2017 | Hornby | A61H 3/008 |
| 2018/0126198 | A1 * | 5/2018 | Troy | B66F 11/044 |

\* cited by examiner

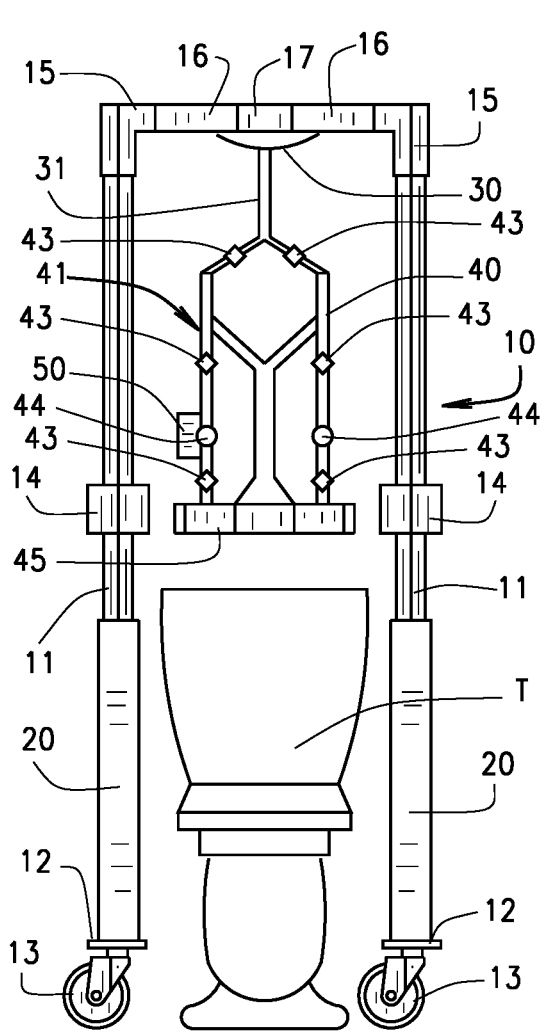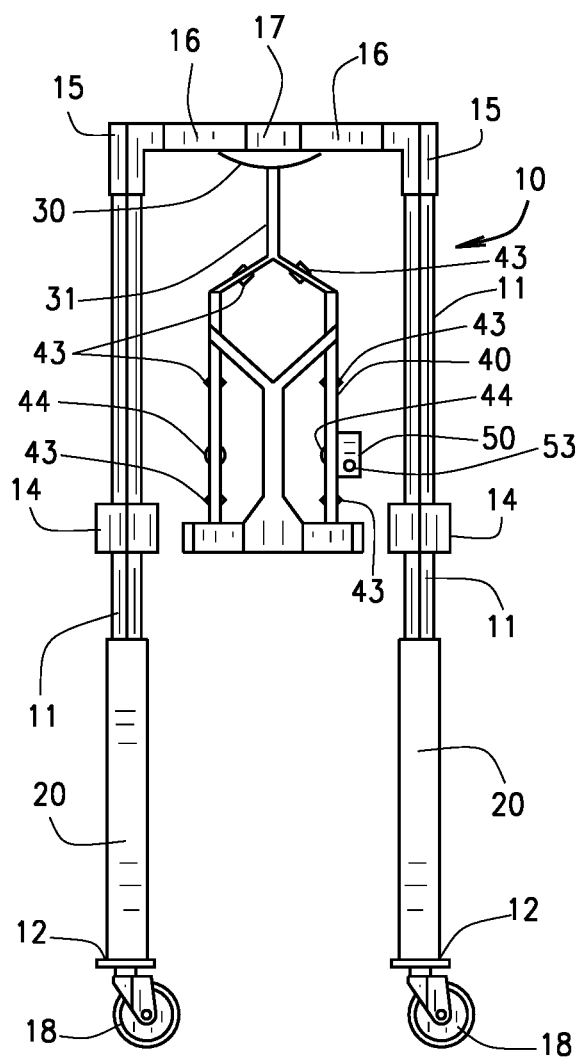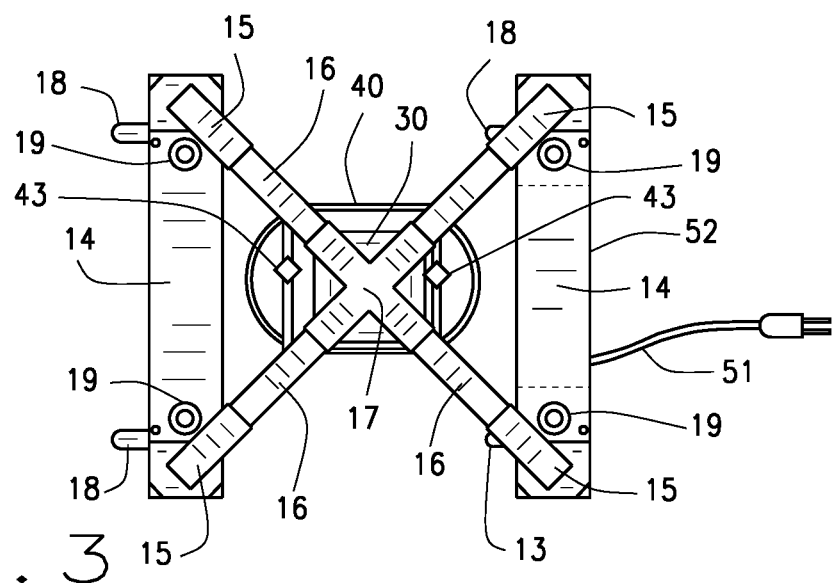

FALL ARRESTING LIFT MACHINE

CROSS-REFERENCE TO RELATED APPLICATION

This non-provisional application claims priority to the pending provisional application Ser. No. 62/934,913 filed on Nov. 13, 2019 and all applications are owned by the same inventors.

BACKGROUND OF THE INVENTION

The present invention relates to equipment suitable for lifting person in a residence. The fall arresting lift machine has particular utility in regulating sitting and standing of a person upon a toilet.

Akin to other creatures, people urinate and defecate as part of living. People take care of those bodily tasks as discretely as possible. From the mists of time, people eliminated waste where they could, and could tolerate. Usually, that was in the woods or outside of a village. In some situations, people of one group left their waste in one place to throw off the trackers of another group. As the waste has its unpleasant smells, sounds, and texture, people sought to distance themselves from their waste. However, people were not also successful in doing so as shown by the epidemics of history that spread through poor sanitation.

In recent centuries, people developed devices and methods to make waste elimination more convenient. For example, chamber pots appeared along with developments in metal working. Chamber pots retained liquid or near liquid waste often during the night that a person would empty the next day. People would also dig trenches to receive waste. With better tools, people also dug latrines that accepted larger quantities of waste. About two centuries ago, people developed the outhouse. The outhouse provided an enclosure above an opening to a pit below that received waste. The outhouse had a location away, and downstream from any residence or cooking arrangement.

With the appearance of municipal and other water systems, people developed toilets and indoor plumbing with all of its advantages and improvements over the past. Sanitation improved and population densities increased. Cities expanded and bottomlands became valuable for wastewater treatment facilities. However, people still used a toilet much as they had done for centuries by sitting upon it.

Time takes its toll on people as does illness, injury, and infirmity at any age. While most people can use a toilet following their training, the aged, the ill, the wounded, and the infirm may have difficulty using a toilet to eliminate waste. A person has to bring herself to a toilet, to orient herself at the toilet, to sit upon the toilet, to use the toilet, and then to stand and depart from the toilet. Each of those tasks presents risks to a person not quite able to move herself fully as she once did.

On a global scale, injuries resulting from falls present a significant and growing problem. As people age, they have an increased risk of falling and suffering serious injury. This risk compounds from more people keeping an active lifestyle later in life than ever before, increasing the opportunity for such an injury. Following a patient's admission to a rehabilitation facility or nursing home, because of mobility impairment from a prior injury or of age and weakness, falls complicate and exacerbate a patient's health care needs.

The high number of falls each year in this country and around the world, coupled with the physical, mental, and financial expenses of these falls, suggests plenty of opportunity for inventions to assist in patient mobility.

DESCRIPTION OF THE PRIOR ART

Over the decades, facilities have installed stalls and handrails to assist people with toileting. But a person must still have strength to move herself through the toileting tasks. For brevity in this description, it uses disabled for the aged, the ill, the wounded, and the infirm. Where this description uses a feminine pronoun, it also includes a masculine pronoun by implication. The disabled have to grasp a handrail near a toilet and then move themselves. Such movements may be difficult or impossible for a disabled person.

Traditional mobility-assist devices used by rehabilitation facilities have limits in their ability to improve the daily life or healing of a patient, and they have limits for protecting the health care workers from injury themselves. Hospital lifts aid in transferring patients from bed to gurney but lack mobility and ease of use while providing no independence for a patient. Wheelchairs provide patients with some unassisted mobility within a facility but call for assistance getting into and out of the wheelchair. Also, rehabilitation patients using wheelchairs tend to regain mobility and balance more slowly due to muscle atrophy in their legs and core.

In recent years, industry has produced walkers. Walkers provide a portable stable platform for a disabled person to use while walking. To some degree, a walker provides a platform where a disabled person may lower herself. Similar to handrails, a walker though requires a disabled person to have enough strength for moving herself. Such movements may be difficult or impossible for some disabled people.

The patent to Kelsey, U.S. Pat. No. 5,273,502 describes a therapeutic unloading apparatus and method. This device has a winch that maintains a steady pull while the load fluctuates as a patient moves in the device.

The patent to Higer, U.S. Pat. No. 5,526,893 shows a physical therapy apparatus. This device has an adjustable sling within side frames on legs of steel tubing. A battery powers a concealed motor.

Turning to the publication to Harris, No. 2004/0063550 it shows a mobile body suspension exercise device. This device shows an arc shaped frame with wheel frames at each end and wheels on axles at the ends of each frame. A winch receives power from its battery to raise and to lower a person in the device.

Then the patent to Martin, No. 02828 provides a weight offloading apparatus with a frame on two legs where each leg has a steerable caster and a fixed caster. A rope routes through five pulleys and on an end of the rope, an elastic cord accommodates fluctuations in rope tension imparted by a patient.

Hawkes then has U.S. Pat. No. 6,935,353 for his mobile rehabilitative walker. This walker has a support frame with one open end and that rests upon wheels and comes with a harness.

The patent to Bergh, U.S. Pat. No. 1,611,807 illustrates an exercising device of a frame on wheels with a crossbar that has straps or slings.

Swan then shows in U.S. Pat. No. 4,256,098 a safety restraint system for ambulatory patients. This system has a tether upon an inertial reel along an overhead track.

The patent to Clark, U.S. Pat. No. 9,814,644 shows a lifting device and associated methods. This device has a main body and a detachable top member where the top member has a winch while the main body folds for carrying.

The prior art provides fixed and portable supporting surfaces that a disabled person may grasp and move herself. But, a disabled person with limited strength to stand and to sit, faces limited selection of devices to assist her with toileting tasks: to approach a toilet, to orient herself at the toilet, to sit upon the toilet, to use the toilet, and then to stand and depart from the toilet. The Fall Arresting Lift Machine overcomes the above-mentioned disadvantages and drawbacks of the prior art. As such, the general purpose of the present invention, which will be described subsequently in greater detail, is to provide a new and improved Fall Arresting Lift Machine which has all the advantages of the prior art mentioned heretofore and many novel features that result in Fall Arresting Lift Machine which are not anticipated, rendered obvious, suggested, or even implied by the prior art, either alone or in any combination thereof.

SUMMARY OF THE INVENTION

The Fall Arresting Lift Machine has a gantry upon wheels, a power source upon the gantry, a motor upon the gantry in communication with the power source, a controller in communication with the motor and the power source, a strap paying out from the motor, a harness upon the strap, and the harness is suitable for wearing by a user. The gantry includes feet, uprights, elbows, braces, and a union. The harness has straps for over both shoulders of the user and a belt. The motor and controller cooperate to assist a user to sit and to stand, and detect abrupt acceleration typical of a fall and arrest the fall. The wheels may swivel, or alternately a portion of the wheels remain in fixed orientation.

There has thus been outlined, rather broadly, the more important features of the invention in order that the detailed description thereof that follows may be better understood and in order that the present contribution to the art may be better appreciated. Additional features of the invention will be described hereinafter and which will form the subject matter of the claims attached.

The present invention solves the previously described critical and growing problems in the rehabilitation and nursing home settings. The present invention includes an algorithm that will characterize a person's normal walking gait and continuously analyze movement relative to this baseline to detect and to predict the onset of a fall. The components of the present invention cooperate to prevent or to arrest a fall. The present invention device aims to offer confidence, independence, and peace of mind to patients in rehabilitation hospitals and nursing homes.

The present invention has its sizing and arrangement such that it will fit through the standard doorframes of rehabilitation facilities and around a toilet. The present invention has its majority of its weight in the lower portion of the device where locates the rechargeable battery, the motor, and the mechanism that stabilizes the patient during a fall event. The casters of the invention move smoothly over flat surfaces and the brakes will stop rotation and translation independently and simultaneously.

Walking gait has undergone study by many, historically by using data from sensors placed on a test subject's legs. The present invention employs a gait analysis in its machine learning algorithms, a part of Artificial Intelligence, or AI, to control the invention. The invention deploys its complex gait analysis into a practical, useful product benefiting a significant segment of society. Additionally, the present invention, through its harness, uses signals from the patient's torso region as input to these algorithms, a more practical yet complicated area from which to draw gait signals than from a patient's legs.

The present invention overcomes challenges in identifying the deviations from normal walking motion that signal an impending fall. The present invention begins with a definition of what constitutes a fall. Many types of falls and many near-fall conditions call for consideration. Health care staff and patients both struggle to define what constitutes a fall. The present invention includes a definition of a fall within the parameters of its algorithm and detects a fall using machine learning techniques.

The present invention also seeks to define a patient's normal walking gait via torso movement rather than leg motion. For practical use in a mobility-assist device, the invention records many signals much more easily from the patient's torso via a harness that the patient would wear as part of the fall arrest apparatus than from the patient's legs.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and devices for carrying out the several purposes of the present invention. It is important, therefore, that the claims be regarded as including such equivalent constructions insofar as they do not depart from the spirit and the scope of the present invention.

It is therefore an object of the present invention to provide a new and improved Fall Arresting Lift Machine that a user may enter and then move easily.

Another object of the present invention is to provide a Fall Arresting Lift Machine that offers individuals the ability to independently walk and transition between sitting and standing.

Still another object of the present invention is to provide a Fall Arresting Lift Machine that liberates vulnerable patients from the fear of falling and restores their dignity as they tend to daily needs such as bathroom use without supervision.

Still another object of the present invention is to provide a Fall Arresting Lift Machine that reduces the risk of falling in persons with mobility limitations initially in longer-stay rehabilitation facilities.

Still another object of the present invention is to provide a Fall Arresting Lift Machine that see uses in physical therapy and professional sports.

Still another object of the present invention is to provide a Fall Arresting Lift Machine that has a calibrated motor and controller that lessen abrupt acceleration from a user's fall.

Still another object of the present invention is to provide a Fall Arresting Lift Machine that keeps patients safe and confident as they perform ADL and heal from injury.

Still another object of the present invention is to provide a Fall Arresting Lift Machine that may be easily and efficiently manufactured and marketed to the consuming public.

Still another object of the present invention is to provide a Fall Arresting Lift Machine that utilizes signals from torso, or harness, inertial measurement units, IMUs to detect falls.

Still another object of the present invention is to provide a Fall Arresting Lift Machine with comparison results that the torso signals eliminate the need for leg signals by providing strong and consistent correlation between the two locations.

Still another object of the present invention is to provide a Fall Arresting Lift Machine that minimizes the number of IMUs upon it.

Still another object of the present invention is to provide a Fall Arresting Lift Machine that establishes normalized gait profiles for each patient.

Still another object of the present invention is to provide a Fall Arresting Lift Machine that benefits a wide variety of motion and mobility areas including rehabilitation, physical therapy, amateur sports, and professional sports.

Still another object of the present invention is to provide a Fall Arresting Lift Machine that seeks commercial success as it fulfills a known need.

Still another object of the present invention is to provide a Fall Arresting Lift Machine that has its deployment to rehabilitation hospitals places as a more controlled environment than that of a standard skilled nursing home as it provides healing patients with a means of safely growing stronger and more independent.

Still another object of the present invention is to provide a Fall Arresting Lift Machine that may be easily and efficiently manufactured and marketed to the consuming public.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

In referring to the drawings,

FIG. 1 is a front view of the preferred embodiment of the present invention;

FIG. 2 is a rear view of the invention;

FIG. 3 shows a top view of the invention;

The same reference numerals refer to the same parts throughout the various figures.

DESCRIPTION OF THE PREFERRED EMBODIMENT

Figure 4:
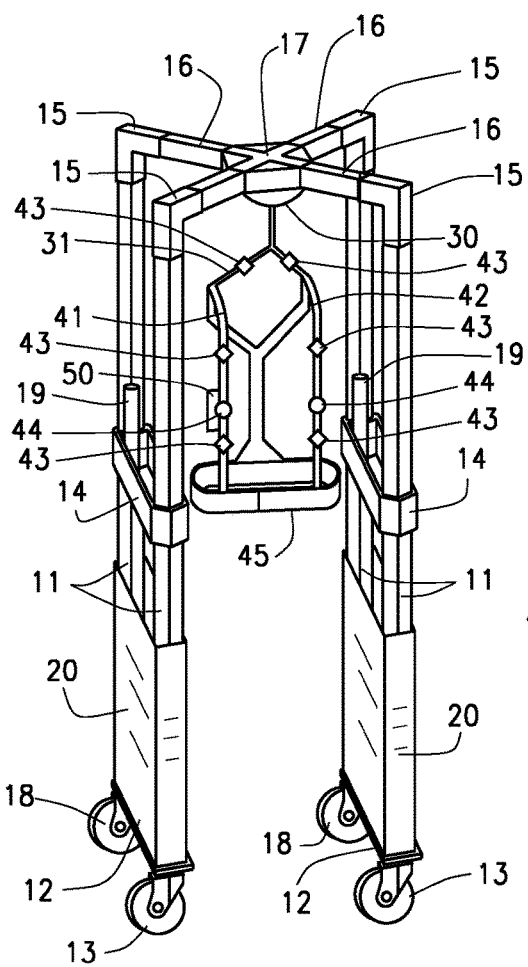
FIG. 4 illustrates a front, top perspective view of the invention.

Referring now to the drawings, and particularly to FIGS. 1-5, a preferred embodiment of the Fall Arresting Lift Machine of the present invention is shown. In FIG. 1, the present invention appears in a front view and has a gantry 10 shown positioned around a typical toilet T. The gantry has four mutually parallel and spaced apart uprights 11, this figure shows two. The two uprights shown have a spacing greater than the width of the toilet T. The two uprights have a length greater than the height of a disabled person, elderly, patient, or user. The two uprights 11 extend into housings 20, one on the left of the figure and the other on the right of the figure. The housings extend downwardly and shown join to feet 12. Each foot 12 receives a housing and contains the uprights one in the foreground and a second, not shown in this figure, in the background. Each foot has a flat, planar shape, with a length to support spacing of uprights from the front to the back in this figure. Beneath the foot, an upright has a caster 13, here shown swiveling to the side that may rotate relative to the longitudinal axis of the upright.

Upwardly from the housing, foot and the casters, each upright joins to a rest 14 here shown on end. The rest spans into the plane of the figure to a second upright, not shown. Each upright continues upwardly from the rest to its length and connects to an elbow 15. Each elbow has a right angle shape, here shown extending inwardly to the gantry. Outwardly from the elbow, thus inwardly from the upright, the gantry has a brace 16 extending perpendicular to the upright. A brace extends from each elbow and thus four elbows and four braces cooperated with the four uprights to form the gantry. The braces extend inwardly towards the center of the gantry and connect to a union 17.

Beneath the union, the gantry 10 pays out a vertical strap 31 from a drive 30. The drive and strap cooperate to lower a user, to raise a user, and to arrest a fall of a user. Because of that, the strap and drive have sufficient strength to support the weight of a user, multiplied by a factor of safety. The strap descends from the drive 30 and has a spaced linkage to a harness 40. The harness fits upon the torso of a user in a comfortable, yet supportive manner. More particularly, the harness has a right strap 41 and an opposite left strap 42. These straps extend from a user's shoulders down the front of the user's rib cage. The straps have sufficient length to reach a belt 45 here shown at the level of the rests 14 in this figure. Alternatively, the straps extend to a seat, or a chair, or other device that grips the hips of a patient. The right strap 41 also has a controller 50, or control system, upon it. The controller includes buttons upon it for a user, or a caregiver, to press and thus operate the invention. The controller has a wired connection to the drive 30, or alternately a Wi-Fi connection.

The harness 40 connects to the vertical strap 31 that further connects to the gantry. The harness uses a similar closure, or buckle, as a U.S. Dept. of Transportation approved passenger auto seat belt but with a proximity sensor 44 to communicate to a programmable logic controller, 53, or PLC. The sensor 44 in coordination with the PLC 53 identifies that the patient has a proper position within the device. The invention has inertial measurement units 43, or IMU, fixed upon the harness in approximate locations as shown. Each strap 41, 42 has three IMU and alternatively a proximity sensor 44 upon it. The belt 45 may also have a proximity sensor thereon. The IMU are manufactured by Inertial Sense, Inc. of Lindon, UT among other manufacturers. During usage, facility staff setup the device and inspect that the device fits upon a user when the user enters a longer-stay rehabilitation hospital or other facility. The facility staff performs this set-up within twenty minutes.

The present invention also focuses on gait capture and sensor placement on the harness. Through this harness placement of the IMU, the invention establishes how the harness sensors cooperate and characterize the movement of the user.

The present invention captures a periodic signal from a walking gait using the inertial measurement units 43 attached to the straps of the harness 40 worn on the user's torso during usage. The invention more particularly, captures walking gait using the IMUs 43 on the harness, particularly its straps 41, 42 upon the user's torso. The present invention then adjusts the IMU locations to those solely on the user's torso as shown in FIGS. 1, 2. The torso data leads to a signal that sufficiently characterizes gait as managed through the PLC 53 and the controller 50. The output of these sensors establishes a periodic "standard signal" indicative of a normal walking gait for a user. The present invention optimizes IMU placement upon the harness resulting in the locations shown.

Though the prior art has used inertial measurement units placed on the legs to capture gait, the present invention utilizes IMU placement upon a user's torso confirmed by statistically significant sampling. The signals from the IMUs 43 of each gait sample undergo analysis and comparison for variation utilizing the PLC 53 and the controller 50. Gait variations from different times of day occur due to fatigue or stress of the user. The present invention with its torso located IMUs demonstrates accurate capture of a user's gait and provides a normalized baseline for fall detection. Outputs from the harness IMUs 43 undergo examination and comparison to each other to confirm their optimal sensor locations for each user. The present invention prefers the strongest signals from torso located IMUs and those with the best correlation to the leg-mounted IMUs. The invention has a number of IMUs from 2 to 18 and preferably from 3 to 6 IMUs. The signals from each IMU undergo examination to identify those sensor locations best suited for capturing a user's walking gait. The IMUs on the harness establish a gait profile for each user based on the outputs of the IMUs. The gait profile accounts for variations that occur throughout a normal day.

Along with gait analysis and management, the controller 50 and its PLC 53, also coordinate the braking system upon at least one caster 13. Based upon gait analysis and prompt detection of a fall event, the PLC 53 locks at least one caster 13 and wheels 18 to prevent rotation and translation of the invention during an adverse event, unauthorized usage, or improper usage.

Turning the invention around, the gantry appears from the rear in FIG. 2. This figure shows the other two uprights 11 opposite those uprights previously shown in FIG. 1. These two uprights shown are mutually parallel and spaced apart. The spacing permits the gantry to fit around a toilet as previously shown. The two uprights extend upwardly from the housings 20 above the feet 12 shown towards the bottom of the figure and the feet have wheels similar to those shown in FIG. 1. In the preferred embodiment, at least one caster has a braking system operatively connected thereto. Optionally, the braking system may have control from a handle 19, or a joystick, upon a rest located proximate the hand of a user. As an alternate embodiment, the wheels here in FIG. 2 have a fixed orientation, and thus have a lockable construction, as at 18. In an alternate embodiment, the user actuates the braking system using the controller. In a further alternate embodiment, the user actuates the braking system from a grip on a pull strap suspended from the gantry and operatively connected to the braking system. The user may also actuate other controls for the invention from one of the rests 14.

These two uprights shown 11 complement the other two uprights so that the gantry 10 rests upon two casters 13 and two wheels 18, upon a supporting surface, such as a bathroom floor, not shown. Similar to FIG. 1, these two uprights shown also connect to the rests 14 and then the elbows 15 opposite the wheels. The elbows then join to the braces 16 that then mutually convene at the union 17. The uprights, elbows, and braces connect and resist the bending moment imparted from the union to the braces and then the elbows. Preferably, the union and the braces deflect less than 1% when under load. Beneath the union, the gantry 10 has its drive as before.

The drive includes a motor and related gearing and with those the drive guides a user through three motions. When a user desires to sit, the user dons the harness, depresses a button on the controller, and the drive pays out strap at a user comfortable rate from about 0.1 to about 6 inches per second. Generally, the strap payout rate follows a typical user descent speed while supporting at least 25% of the user's body weight. When the drive detects a slackening of the strap tension, the drive then recognizes the user has seated herself and then shuts off. Then when a user desires to stand from a seated position, the user checks, or dons, the harness, depresses another button on the controller, and the drive reels in strap at a user comfortable rate of from about 0.1 to about 6.0 inches per second. Generally, the strap reel in rate slightly accelerates a typical user's ascent speed while supporting at least 33% of the user's body weight. When the drive detects a tightening of the strap tension further, the drive then recognizes the user has stood up and then shuts off. Alternatively, when the drive detects the strap is parallel to an upright, the drive recognizes the user has attained a standing position.

When a user wears the harness and has seating movement, a standing movement, or a combination of them, a user may fall from various causes. During the fall, the user accelerates from gravity and imparts an impulse of tension to the strap, or an abrupt tensioning. The drive monitors strap tension and upon detecting a tension impulse, typically over 0.40 g, 40% gravity, —that is a fall—the drive abruptly slows paying out strap or reeling in strap, and eventually stops the vertical strap entirely. The drive effectively applies a reaction force to the vertical strap of magnitude and direction to arrest a fall of a patient. The drive includes a strap tension sensor or accelerometer for this safety function. The drive's safety components remain contained within the drive so that a user may not disable them. The drive has an electrically powered motor in communication with the power source. The drive effectively engages the motor upon detecting an abrupt tensioning of the vertical strap in particularly and the motor operates at a variable speed that slows the fall of a user gradually.

In this figure, the right strap 41 has the controller 50 as before. The controller has the PLC in electrical communication to it. The controller has the PLC 53 operatively connected to it, here shown in an alternate embodiment location towards the rear of the controller.

Having described the invention as a user would enter it, FIG. 3 shows a top view of the gantry 10. As before, the gantry has four mutually parallel and spaced apart uprights, here shown on end and beneath the elbows 15. The gantry has four elbows 15 here shown near the apparent corners of the invention and extending inwardly and diagonally. Each elbow has a brace 16 extending inwardly to the union 17 shown in the center of the figure. The union has a generally X shape with a hollow form that receives the braces opposite the elbows. In the preferred embodiment, the invention has its drive and related components within a housing proximate a foot. In an alternate embodiment, the invention has its drive 30 beneath the union and the union generally fits within the perimeter of the drive. In the preferred embodiment, below the drive and the union, the invention has its harness 40 generally showing its belt in an oval form in this figure and its two straps outwardly of the union. The harness includes a plurality of IMUs 43 deployed upon its straps. As the union has hollow construction so do the elbows, braces, and uprights. The hollow construction permits passage of the vertical strap 31 for the drive and related wiring for the controller.

Into the plane of the figure beneath each elbow, the uprights extend to rests 14 above the housings 20 concealed beneath the rests. Upon each rest proximate an upright beneath an elbow 15, the gantry has a control 19 here shown as an end of a cylinder. The controls have communication to the controller and allow a user to regulate operations of the present invention.

Concealed beneath each housing, the feet 12 have their paired arrangement as previously shown. The feet have a generally thin rectangular shape. The feet extend through the spacing of a pair of uprights and to the edge of the ends of the uprights. Each foot receives two casters 13 and two wheels 18 may be fixed in an alternate embodiment. Within one housing 20 and upon one plate, here shown to the right of the figure, the invention has its power supply that has a battery 52 and a cord 51 for utility service. The battery is a rechargeable electric battery, such as lithium ion and the like of amperage, wattage, and sufficient energy storage to operate the invention through at least seven sit and stand cycles under a user load. The invention may recharge the battery using the cord 51. In an alternate embodiment, the invention may also operate directly upon utility provided electricity through the cord 51 as it bypasses the battery to directly power the drive and motor.

Looking at the invention from slight above, FIG. 4 then illustrates a perspective view of the invention with its gantry 10. The gantry has its four uprights 11 arranged in two pairs upon two housings 20 with two feet 12 shown beneath them. Each foot has a caster 13, that swivels, in line with an upright and two wheels may be fixed as at 18 in an alternate embodiment. This view shows the gantry ready to receive a user. The user enters between the two pairs of uprights beneath the braces. The X shape of the pattern of braces allows the user to enter the gantry at a wide distance between two braces and corresponding uprights. The pattern of braces also prevents a user from walking into a brace when entering or leaving the invention. The braces 16 extend from the elbows 15 to the union 17 that supports the harness 20 suspended below. The drive pays out and reels in the vertical strap 30 connected to the harness and its two straps 41, 42 with IMUs 43 upon them. The right strap 41, has a controller 50, as before. The strap permits the harness to rotate about the axis of the strap as the user needs during donning of the harness, sitting, standing, and doffing of the harness. The harness has its two straps that extend in a Y like shape from a main strap typically worn upon the back of a user. The straps 41, 42, each have their user specific positioned IMUs 43, typically three per strap. The main strap connects to the belt and the two straps also connect to the belt opposite the main strap and spaced outwardly from the main strap. Toward the background, two uprights have controls 19 shown adjacent to them above the rests. The controls have communication to the controller. The controls have an elongated cylindrical form suitable for grasping by a user. In an alternate embodiment, the controls can be joysticks.

Figure 5:
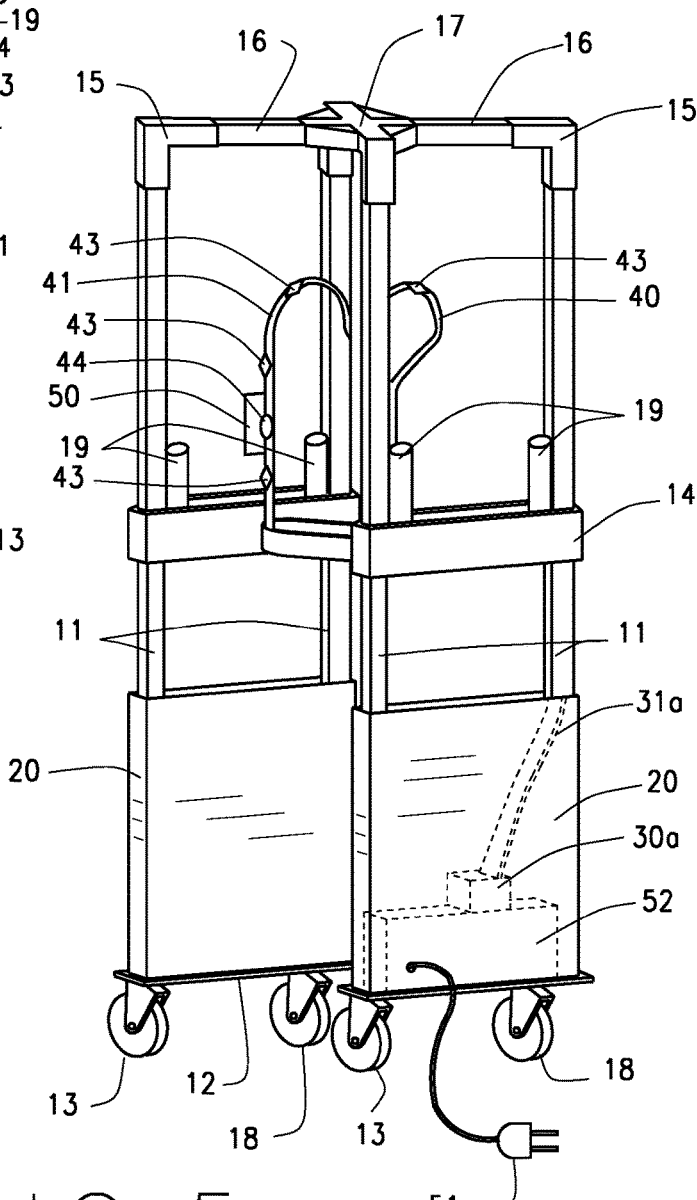
FIG. 5 shows a front, left perspective view of the invention.

And, FIG. 5 shows a second perspective view of the invention with its gantry 10 as before. The uprights 11 appear in their two pairs and extend into their respective housings 20 as shown. Beneath each housing, each pair of uprights connects to a foot 12 with a caster 13 and a wheel 18, beneath the foot and beneath each upright of a pair. One foot 12 within a housing, here shown on the right, supports the battery 52, the cord 51 for utility service, a drive 30a, and a vertical strap 31a paying out from the drive, and related electrical components, including the PLC 53. The vertical strap 31a runs from the drive 30a to the nearest upright 11 for passage upwardly in the gantry to the union and then down to the harness. Preferably the invention operates upon its battery and alternatively upon utility service. Spaced above the housings 20 and well above the feet 12, the invention has its two rests 14 here shown spaced apart and mutually parallel and also spaced above the feet and mutually parallel to them. The rests have their controls 19 extending upwardly and locating proximate each upright. The harness 40 appears within the gantry 10 and its rests 14 ready for a user to don. This figure omits the vertical strap for clear display of the harness. The harness has its two straps suitable for resting upon the shoulders and torso of a user. The straps, as at 41, 42 join to the belt 45. When the invention is ready to receive user, the user, or a caregiver, reels in the vertical strap so that the belt attains a position proximate the rests 14. Here, the figure shows the belt towards the bottom of the rests. This harness position allows a user to fit into the harness and have the rests nearby for the user to grasp one or both rests as needed. Though this description uses vertical strap 31, the Applicants foresee a flexible, slender, elongated member of sufficient strength that may also lift and lower the harness. The Applicants also foresee the drive 30, a motor, power source, battery 52, and utility cord 51 having a location within a housing and proximate to a foot thus lowering the center of gravity of the gantry 10. The drive also includes a winch, a hoist, and the like with suitable mechanism to arrest or to prevent a fall of user in the invention.

As a reminder to the reader, the invention supports a person during usage. The invention has a design loading augmented by a safety factor. But, the invention is not a toy and should be used appropriately for its intended purpose and shown the respect due a machine that lifts a person safely.

While a preferred embodiment of the Fall Arresting Lift Machine has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sturdy material such as plastic, polymer, polyvinyl chloride, high strength nylon, metal, alloy, stainless steel, or composite may be used. The invention has a construction of a sturdy, lightweight material that resists the fluids encountered in a bathroom and thus makes easier the cleaning of the invention by a user or the staff of a facility.

Although providing a machine that sees use in facilities for aged, disabled, or other people has been described, it should be appreciated that the Fall Arresting Lift Machine herein described is also suitable for nursing homes, hospitals, hospice homes, apartments, condominiums, dormitory rooms, houses, offices, facilities, select ships, select mines, and the like where a person needs a little help getting on and getting off a toilet.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Various aspects of the illustrative embodiments have been described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations have been set forth in order to provide a thorough understanding of the illustrative embodiments. However, it will be apparent to one skilled in the art that the present invention may be practiced without the specific details. In other instances, well known features are omitted or simplified in order not to obscure the illustrative embodiments.

Various operations have been described as multiple discrete operations, in a manner that is most helpful in understanding the present invention, however, the order of description should not be construed as to imply that these operations are necessarily order dependent. In particular, these operations need not be performed in the order of presentation.

Moreover, in the specification and the following claims, the terms "first," "second," "third" and the like—when they appear—are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to ascertain the nature of the technical disclosure. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

We claim:

1. A machine for arresting falls and lifting a person, comprising:
    a gantry, said gantry having four uprights arranged mutually parallel and vertical, said four uprights organized into two pairs;
    at least one housing, said at least one housing receiving a pair of said uprights;
    each pair of uprights having a foot and at east one caster beneath the foot opposite the uprights;
    each upright having an elbow extending inwardly of said machine from each upright opposite said foot;
    each elbow connecting to a brace further extending inwardly;
    a union receiving each of said braces;
    a vertical strap descending from and retracting to said union, said vertical strap connecting to a harness, said harness adapted to fit upon a torso of a person, said harness having a plurality of inertial measurement units thereon and at least one proximity sensor thereon;
    wherein a drive pays out said vertical strap in a controlled manner and reels in said vertical strap in a controlled manner and wherein said drive detects abrupt tensioning of said strap and imparts a counteracting tension to the strap to arrest a fall of a person;
    a power source; and
    a controller accessible to a person.

2. The machine for arresting falls and lifting a person of claim I further comprising:
    said drive having a tension sensor and an accelerometer detecting any abrupt tensioning of said strap denoting a fall event of a person and upon detecting abrupt tensioning said drive imparts a reaction force to said strap;
    said drive having electrical communication with said power source and with said controller: and
    wherein said power source is one of a lithium ion battery and a cord adapted to connect to utility service.

3. The machine for arresting falls and lifting a person of claim 2 further comprising;
    said drive having an electrically powered motor in communication with said power source; and
    said drive engaging said motor upon detecting an abrupt tensioning of said strap and said motor operating at a variable speed adapted to slow the fall of a person gradually.

4. The machine for arresting falls and lifting a person of claim 3 further comprising:
    said tension sensor and said accelerometer cooperatively detecting an abrupt tensioning of said vertical strap in excess of 0.40 g.

5. The machine for a sting falls and lifting a person of claim 3 further comprising:
    said drive, said tension sensor, and said accelerometer being in operative communication with said drive; and
    said drive reeling in said vertical strap at a rate from about 0.1 inches per second to about 6 inches per second.

6. The machine for arresting falls and lifting a person of claim 2 further comprising:
    a braking system upon at least one caster, said braking system communicating with said controller;
    at least one control operatively communicating with said braking system;
    two rests, each rest spanning between a pair of said uprights and locating above one of said housings; and
    said at least one control locating upon said rest and is adapted to receive a hand of a person.

7. The machine for arresting falls and lifting a person of claim 2 further comprising:
    said controller having a programmable logic controller and including said tension sensor and said accelerometer;
    said controller having communication with said drive and said power source.

8. A device that follows the gait of a person comprising:
a harness adapted to fit upon a torso of a person, said harness having two straps, each of said straps having at least two inertial measurement units and at least one proximity sensor thereon, and a vertical strap joining to said straps;
a controller upon one of said straps, said controller being in electrical communication with said inertial measurement units and said proximity sensor and being accessible to a person;
said vertical strap connecting to a drive wherein said drive pays out said vertical strap in a controlled manner and retracts said vertical strap in a controlled, manner and wherein said drive detects abrupt tensioning of said strap and imparts a counteracting force to the strap to arrest a fall of a person;
a mobile gantry connecting to said vertical strap above said harness, said gantry is adapted to have a height greater than that of a person; and
a power source in electrical communication with said harness, said controller, and said drive.

9. The device that follows the gait of a person of claim 5 further comprising:
said controller having a programmable logic controller, a tension sensor, and an accelerometer;
said controller having communication with said drive and said power source; and
said programmable logic controller being in communication with said at least two inertial measurement units and said at least one proximity sensor.

10. The device that follows the gait, of a person of claim 9 further comprising:
at least two controls within reach of a person, said at least two controls in electrical communication with said controller wherein a person may operate said device.

* * * * *